United States Patent
Nouaille et al.

(10) Patent No.: US 11,149,230 B2
(45) Date of Patent: Oct. 19, 2021

(54) PROCESS FOR EXTRACTING CARBOXYLIC ACIDS PRODUCED BY ANAEROBIC FERMENTATION FROM FERMENTABLE BIOMASS

(71) Applicant: AFYREN, Saint Beauzire (FR)

(72) Inventors: Regis Nouaille, Cournon d'Auvergne (FR); Jeremy Pessiot, La Charite sur Loire (FR)

(73) Assignee: AFYREN, Saint Beauzire (FR)

( * ) Notice: Subject to any disclaimer, the term of this patent is extended or adjusted under 35 U.S.C. 154(b) by 437 days.

(21) Appl. No.: 15/213,530

(22) Filed: Jul. 19, 2016

(65) Prior Publication Data

US 2017/0022446 A1 Jan. 26, 2017

(30) Foreign Application Priority Data

Jul. 23, 2015 (FR) .................. FR1556976

(51) Int. Cl.
| | | |
|---|---|---|
| *C12P 7/40* | (2006.01) | |
| *C12P 7/64* | (2006.01) | |
| *C11B 3/00* | (2006.01) | |
| *C12P 7/42* | (2006.01) | |
| *C07C 51/48* | (2006.01) | |
| *C11B 3/12* | (2006.01) | |
| *C12M 1/00* | (2006.01) | |

(52) U.S. Cl.
CPC .............. *C11B 3/006* (2013.01); *C07C 51/48* (2013.01); *C11B 3/12* (2013.01); *C12M 47/10* (2013.01); *C12P 7/42* (2013.01)

(58) Field of Classification Search
CPC ......... C12P 7/42; C07C 51/48; C07C 53/126; C07C 53/124; C11B 3/12; C11B 3/006
See application file for complete search history.

(56) References Cited

U.S. PATENT DOCUMENTS

| | | | | |
|---|---|---|---|---|
| 2009/0227003 | A1* | 9/2009 | Blotsky | ............... C12M 21/02 435/257.1 |
| 2014/0073820 | A1* | 3/2014 | Bazzana | ............... C12M 21/12 568/913 |
| 2014/0178951 | A1* | 6/2014 | Ross | ..................... C07C 51/48 435/134 |

* cited by examiner

*Primary Examiner* — Satyendra K Singh

(57) ABSTRACT

The process involves extracting carboxylic acids having from one to nine carbons, the carboxylic acids produced by microorganisms in a fermentation reactor by anaerobic fermentation from fermentable biomass. The extraction is a liquid-liquid type, and includes
  a) choosing an endogenous extraction solvent among at least one of the carboxylic acids, such that the number of carbons of the solvent is greater than or equal to the number of carbons of the carboxylic acid to be extracted,
  b) bringing the extraction solvent chosen into contact with the fermentation medium, without interrupting the fermentation, outside the fermentation reactor,
  c) separating (6) the fermentative metabolites from the extraction solvent by at least one distillation, and
  d) collecting and storing or using the fermentative metabolites obtained in step c).
The invention also relates to a facility for carrying out the process.

9 Claims, 1 Drawing Sheet

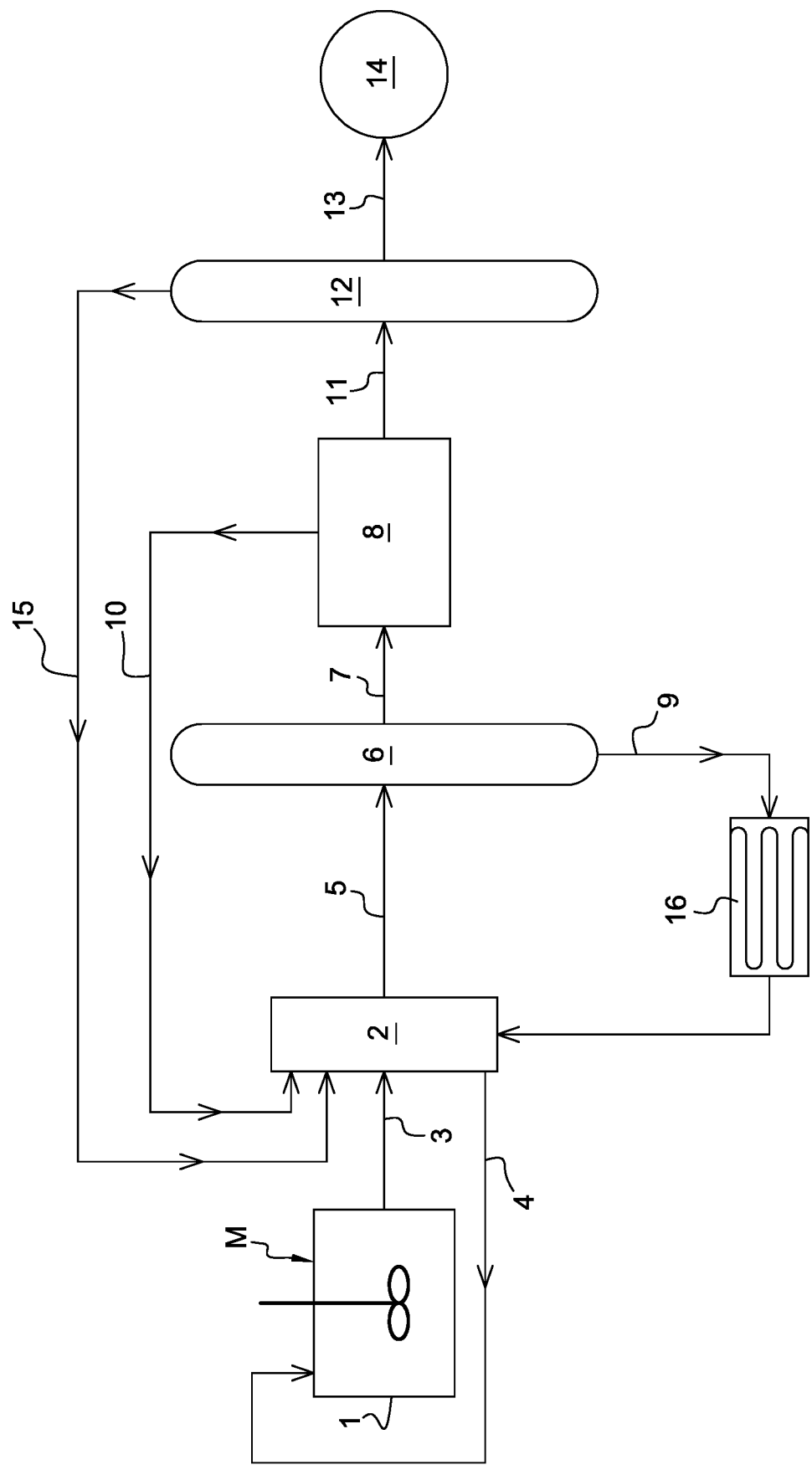

PROCESS FOR EXTRACTING CARBOXYLIC ACIDS PRODUCED BY ANAEROBIC FERMENTATION FROM FERMENTABLE BIOMASS

BACKGROUND OF THE INVENTION

The present invention relates to a process for extracting carboxylic acids produced by anaerobic fermentation from fermentable biomass. The process is particularly intended for liquid-phase carboxylic acid extraction.

The term "fermentable biomass" denotes herein an organic, advantageously non-food, substrate obtained from waste, by-products and coproducts formed from organic matter, i.e. biomass resulting from human activities, whether domestic, industrial, agricultural, forestry, aquaculture or food-processing activities, or derived from farming. By way of nonlimiting examples, mention may be made, as organic substrate, of dung, the organic fraction of household waste, abattoir coproducts, cellulosic and lignocellulosic residues originating from the food-processing industry, such as those derived from the conversion of sugar cane (bagasse), of sunflower or of soya.

The term "anaerobic fermentation" is intended to mean a fermentation carried out under anaerobic conditions by eukaryotic or prokaryotic microorganisms, such as bacteria, fungi, algae or yeasts.

Among fermentative metabolites, carboxylic acids are fermentative metabolites termed precursors, it being understood that other fermentative metabolites are also termed precursors. By way of nonlimiting example, mention may be made of acetic, propionic, butyric, valeric, caproic, heptanoic, octanoic, nonanoic and phenylacetic acids. These precursors subsequently allow the production of molecules which are of greater energy and/or chemical interest, it being understood that they are organic molecules. As molecules which are of energy and/or chemical interest, mention may be made, for example, of molecules which have a carbon-based chain, such as acids, hydrocarbons, methane, esters, alcohols, amides or polymers.

Subsequently, reference will be made to carboxylic acids, it being understood that the invention applies to the extraction of fermentative metabolites in general. Carboxylic acids, and in particular volatile fatty acids or VFAs, can be converted, for example, to ketones, alkanes, alcohols and alkenes. It is understood that such a fermentation also produces metabolites other than carboxylic acids, in greater or lesser amount. Mention may be made, inter alia, of esters, gases, lactic acid, alcohols, hydrogen and carbon dioxide. It is, moreover, known that the production of carboxylic acids carried out by anaerobic fermentation induces acidification of the medium which is prejudicial to microorganisms. Since acidification of the medium induces inhibition of the microorganisms, and therefore a slowing down or even an arrest of fermentation, it is necessary to work batchwise. For this, the carboxylic acids are extracted during a distinct step, after a given fermentation time. Such an extraction does not therefore allow rapid and continuous production of "precursor" modules, the yield not being optimal. Furthermore, such a batchwise extraction process consumes microorganism strains and generates waste with low or no exploitability. It is advantageous to optimally extract the carboxylic acids produced by anaerobic fermentation without inhibiting the microorganisms. A process for extracting a given metabolite, in the case in point butanol, using an extraction solvent comprising a carboxylic acid, is known from WO-A-2011/063391. The solvent is a commercially available solvent. A process for treating water which makes it possible to extract organic compounds, including amines, amino acids and phenols, using as solvent an organic solvent, in the case in point a liquid and water-immiscible carboxylic acid, in order to obtain an organic phase and an aqueous phase, is also known from FR-A-2 591 505. It proves to be the case that these processes are not suitable for the extraction of metabolites, such as carboxylic acids, continuously produced by fermentation.

BRIEF SUMMARY OF THE INVENTION

The invention is more particularly aimed at remedying these drawbacks by providing an extraction process which makes it possible to produce in a continuous, biocompatible, regular and controlled manner and with a minimum of non-exploitable waste and without inhibiting the microorganisms, various "precursor" fermentative metabolites obtained by anaerobic fermentation.

To this effect, a subject of the invention is a process for extracting carboxylic acids having from one to nine carbons, produced by microorganisms in a fermentation reactor by anaerobic fermentation from fermentable biomass, said extraction being of liquid-liquid type, which comprises at least the following steps:
  a) choosing an endogenous extraction solvent among at least one of the carboxylic acids produced during anaerobic fermentation, such that the number of carbons of the solvent is greater than or equal to the number of carbons of the carboxylic acid to be extracted, having a density below that of water and the boiling point of which is above 70° C. under normal conditions of pressure,
  b) bringing the extraction solvent chosen into contact with the fermentation medium, without interrupting the fermentation, outside the fermentation reactor,
  c) separating the fermentative metabolites from the extraction solvent by means of at least one distillation,
  d) collecting and storing or using the fermentative metabolites obtained in step c).

Such a process makes it possible to continuously extract fermentative metabolites, while preserving the production capacity of the microorganisms present in the bioreactor.

The term "endogenous" should be understood as denoting a compound, or a mixture of compounds, which is (are) produced, but nonexclusively, by anaerobic fermentation. In other words, the endogenous solvent may be produced by other routes which result in a product which is similar, if not identical, to that produced during the anaerobic fermentation, this being regardless of the amounts produced.

The extraction step makes it possible not only to continuously collect the molecules produced in the fermentation reactor, but also to preserve the microorganisms responsible for this production, the extraction being carried out, by virtue of the endogenous solvent, under conditions which are non-lethal for all of the microorganisms, i.e. under biocompatible extraction conditions. In this way, problems associated with the accumulation of the precursors in the fermentation reactor are dispensed with, for example the acidification of the fermentation medium by accumulation of the carboxylic acids produced which are harmful to the microorganisms. The activity of the microorganisms is maintained at a high level, close to the initial level, throughout the fermentation cycle.

According to advantageous but non-obligatory aspects of the invention, such a process may comprise one or more of the following characteristics:

In step a), the endogenous extraction solvent is a carboxylic acid having at least four carbons.

After step c), and before step d), the carboxylic acids are separated, by distillation, during an additional step e), from the water of the organic phase obtained in step c).

The extraction solvent is a carboxylic acid having from four to nine carbons.

The extraction solvent is a carboxylic acid having seven or eight carbons.

The extraction solvent is chosen from heptanoic acid, octanoic acid or nonanoic acid.

An additional decanting step f), between steps c) and d), allows a first separation between the organic and aqueous phases.

During the bringing of the fermentation medium into contact with the extraction solvent outside the reactor, the fermentation medium is taken continuously.

During the bringing of the fermentation medium into contact with the extraction solvent outside the reactor, the fermentation medium is taken sequentially.

After steps b) and c), at least one part of the liquid phase resulting from the extraction is reintroduced into the fermentation reactor and incorporated into the fermentation medium.

The invention also relates to a facility for carrying out a process in accordance with one of the previous characteristics, which comprises at least:

one fermentation reactor, one extraction member suitable for bringing the fermentation medium into contact with the extraction solvent, at least one distillation member.

According to advantageous but non-obligatory aspects of the invention, such a facility may comprise one or more of the following characteristics:

the facility also comprises at least two distillation members and at least one decanting member.

BRIEF DESCRIPTION OF THE SEVERAL VIEWS OF THE DRAWING

The invention will be understood more clearly and other advantages thereof will emerge more clearly on reading the description of several embodiments of the invention, given by way of nonlimiting example and made with reference to the following drawing in which:

FIG. 1 is a simplified diagram representative of one embodiment of the process which is the subject of the invention comprising two distillations and one decanting member.

DETAILED DESCRIPTION OF THE INVENTION

The various steps of the process are now described with reference to FIG. 1, it being understood that the steps known per se are not detailed. It should be noted that FIG. 1 shows a process comprising two distillations, i.e. an embodiment which represents an economically advantageous solution for facilities of common dimensions. A facility with a single distillation station is technically possible and even advantageous, but, in order to be economically advantageous, requires a facility of larger dimensions, such as a facility of the size of those encountered in an industrial refinery.

Moreover, the extraction of carboxylic acids, by way of example, will subsequently be described, it being understood that other fermentative metabolites may be extracted by the endogenous carboxylic acids.

First of all, the substrate S used for the anaerobic fermentation is, advantageously, nontreated, namely it has undergone no physicochemical or enzymatic pretreatment. This substrate S is predominantly made up of fermentable biomass. By way of nonlimiting example, mention may be made of agricultural or plant waste (straw, bagasse, spent corn, weeds, wood, clippings/mowings), paper waste (cardboard, paper), food-processing waste, abattoir waste, the organic fraction of household waste, farming effluents (dung, liquid manure, droppings), algae, aquaculture waste, waste from forestry activity or else fermentable coproducts form the cosmetics industry. Certain substrates contain organic molecules, such as organic acids, which will not influence, or marginally influence, the fermentation process. On the other hand, these molecules may be found in the fermentation medium and may participate, for example, in the production of the defined final organic molecules.

The substrate S is introduced into a fermentation reactor 1, known per se and proportioned for the desired production, whether the latter is on the laboratory scale for carrying out tests or on the industrial scale in the case of a production. In other words, the fermentation reactor 1 or bioreactor has a volume which ranges from a few liters to several hundred cubic meters, as required.

Microorganisms are advantageously initially introduced into the fermentation reactor 1, in an amount sufficient to begin the fermentation. The microorganisms are advantageously inoculated in the form of a consortium, illustrated by the arrow M. The term "consortium" denotes a mixture or mix of eukaryotic and prokaryotic microorganisms, whether they are bacteria, yeasts, fungi or algae. These microorganisms essentially come from natural ecosystems, advantageously but non-exclusively from anaerobic ecosystems such as, by way of nonlimiting example, the anaerobic zone of aquatic media, such as the anoxic zone of certain lakes, soils, marshes, purification sludges, the rumen of ruminants or the intestine of termites. It should be kept in mind that the qualitative and quantitative distribution of the various types and species of microorganisms in the consortium M is not precisely known and especially can vary in large proportions. It proves to be the case that this qualitative and quantitative diversity surprisingly provides a robustness and an adaptability of the microorganisms which make it possible to ensure optimal use of the substrates, whatever the composition of the latter, this being under variable fermentation conditions.

Moreover, because the substrate S is used as it is, i.e. it is not sterilized or, more generally, the microorganisms that it contains are not removed prior to its introduction into the bioreactor 1, it proves to be the case that the microorganisms endemic to the substrate S are, de facto, incorporated into the consortium M or at least combined with the latter in the bioreactor 1.

The microorganism consortium M, combined with the microorganisms possibly present in the substrate 1, allows the fermentation of the substrate S, this being without addition of products such as enzymes. Moreover, the fermentation takes place under anaerobic conditions, more precisely when the redox potential is less than −200 mV, advantageously between −550 mV and −200 mV, and when the pH is less than 8, preferably between 4 and 7. The fermentation is advantageously limited to the production of "precursor" fermentative metabolites, namely carboxylic acids. A reaction similar to the acidosis phenomenon encountered in ruminants is thus induced, while at the same time having a methane production close to zero. Methane is, generally, one of the final fermentative metabolites obtained during anaerobic fermentation by microorganisms derived from natural ecosystems.

The fermentation results, firstly, in the formation of carboxylic acids having from one to nine carbons, mainly from two to four carbons, such as acetic acid, propionic acid and butyric acid. Carboxylic acids with a longer chain, therefore greater than four carbons, are also obtained, such as valeric and caproic, heptanoic, octanoic or nonanoic acids. By continuing the fermentation and/or by increasing the amount of microorganisms in the bioreactor 1, if required with selected microorganisms, it is possible to promote the production of carboxylic acids with a longer carbon-based chain, therefore greater than four carbons.

In other words, the metabolites produced in quantity during the fermentation are essentially carboxylic acids of two to six carbons. Subsequently, the extraction will essentially concern the extraction of these carboxylic acids, it being understood that the process can be carried out for other carboxylic acids or other fermentative metabolites produced during other types of fermentation.

The fermentation can be carried out, preferably, in continuous mode, in batchwise mode or else in fed-batch mode in a single fermentation reactor 1 or in several fermentation reactors 1 arranged in series.

In any event, the fermentation is carried out in order to ensure the production of carboxylic acids, in the liquid phase. Thus, it is easily understood that the fermentation medium comprises a solid phase containing, at least initially, the solid fraction of the substrate S and also the solid fraction of the microorganism consortium M.

The liquid phase of the fermentation medium contains the molecules produced during the fermentation, or fermentative metabolites, and also the liquid fraction of the substrate S, at least at the time of the start of fermentation.

The fermentation time varies, inter alia, according to the substrate S, the microorganisms M present and the fermentation conditions. Typically, the fermentation period is between 1 and 7 days, preferentially between 2 and 4 days. The metabolite concentration obtained in the fermentation medium at the end of this period is variable, but, for carboxylic acids, is generally about from 10 to 20 g/l, according to the carboxylic acids, it being understood that, under certain conditions, it may be greater than 35 g/l, for example in the region of 50 g/l. At the end of the fermentation step, the fermentation medium is at an acidic pH, which is generally between 4 and 6, owing to the presence of the carboxylic acids in the fermentation medium.

When the production of predefined metabolites, for example of carboxylic acids, by fermentation of the substrate S reaches a defined amount, generally in the permanent regime phase of the fermentation, the molecule extraction step is initiated.

Preferably but without obligation, this predefined amount of carboxylic acids corresponds to a slowing of the growth of the microorganisms, and therefore lies in the region of a microorganism inhibition threshold, which is linked to an acidification of the fermentation medium by the carboxylic acids.

The extraction is of liquid-liquid type. The extraction solvent is an endogenous solvent, i.e. a solvent chosen from at least one of the compounds produced during the fermentation. It is understood that the solvent may be a mixture of several compounds produced during the fermentation. In this case the endogenous solvent is chosen from carboxylic acids which are part of the fermentative metabolites.

Indeed, unlike other organic solvents, the carboxylic acids are produced during fermentation. The use of such an endogenous solvent has many advantages.

First of all, the absence of molecules other than those resulting from the fermentation is thus guaranteed: there is no organic solvent which risks being found in trace amounts in the final product.

With the carboxylic acids, it is possible, inter alia, to extract not only carboxylic acids but also other metabolites such as alcohols, amines or amino acids, and aromatic compounds such as phenyl acids. Furthermore, in a liquid-liquid extraction, solvent losses are inevitable. They occur during storage, during distillation or even during fermentation if the solvent is capable of being consumed by the microorganisms. An introduction of solvent is thus required, thereby generating additional costs and restrictions in transportation and in environmental terms.

Using a solvent endogenous to the anaerobic fermentation process, such as a carboxylic acid, makes it possible to at least partially compensate for the solvent losses.

Moreover, such an endogenous solvent avoids any risk of an unwanted and/or uncontrolled reaction between the solvent and not only the volatile fatty acids produced during the fermentation but, more generally, the products resulting from the fermentation.

Finally, the use of a carboxylic acid as solvent contributes to the reduction of the pH of the aqueous phase during the extraction.

The carboxylic acids, produced during the fermentation and used as solvent, that may be present in the fermentation medium are, for example but non-exclusively, acids having from four to nine carbons.

In any event, the carboxylic acid will be chosen such that its number of carbons is greater than or equal to the number of carbons of the metabolite to be extracted.

Nonlimiting examples of such acids produced during the fermentation are given in table 1 hereinafter.

In table 1, the density is given at ambient temperature, in the region of 20° C.

TABLE 1

| | | | |
|---|---|---|---|
| 2-methylpropanoic acid or isobutyric acid | $C_4H_8O_2$ | Density in $g/cm^3$: 0.9681 | Boiling point at atmospheric pressure: 154° C. |
| Methyl ethyl acetic acid or pentanoic acid or valeric acid | $C_5H_{10}O_2$ | Density in $g/cm^3$: 0.9339 | Boiling point at atmospheric pressure: 186° C. |
| Hexanoic acid or caproic acid | $C_6H_{12}O_2$ | Density in $g/cm^3$: 0.9212 | Boiling point at atmospheric pressure: 205° C. |
| Heptanoic acid | $C_7H_{14}O_2$ | Density in $g/cm^3$: 0.9188 | Boiling point at atmospheric pressure: 222° C. |
| Octanoic acid or caprylic acid | $C_8H_{16}O_2$ | Density in $g/cm^3$: 0.9106 | Boiling point at atmospheric pressure: 239° C. |
| Nonanoic acid | $C_9H_{18}O_2$ | Density in $g/cm^3$: 0.900 | Boiling point at atmospheric pressure: 254° C. |

More specifically, the applicant has noted, on the basis of tests performed, that carboxylic acids having six to nine carbons and, advantageously, seven or eight carbons, constitute particularly advantageous endogenous solvents. In other words, from the carboxylic acids mentioned, in a nonlimiting manner and by way of example, in table 1, the applicant has retained caproic, heptanoic and octanoic acids as endogenous solvent. As a variant, it is possible to use the isomers of these acids.

The molecules, and thus in this case the fermentative metabolites, are preferentially extracted individually, or at least extracted in molecular families, from the liquid phase of the fermentation medium, thereby allowing, inter alia, better yields and facilitating the production of specific compounds from these extracted molecules.

In any event, the metabolites which are, at least partially, extracted are extracted under conditions such that the extraction does not destroy and does not inhibit the microorganisms M, or at least extracted in proportions such that this does not substantially modify the continuation of the fermentation by the microorganisms M present in the fermentation medium. In other words, the solvent is not lethal for all of the microorganisms. The extraction does not therefore interfere with, or degrade, the fermentation medium or the fermentative capacities of the microorganisms M that it contains. The extraction is therefore carried out under conditions such that it is biocompatible.

When molecules such as carboxylic acids are extracted from the fermentation medium, the acidification of the fermentation medium by these acids is de facto reduced. Thus, the fermentation, and therefore the production of metabolites, continues under conditions similar to the initial conditions, the fermentation medium remaining not very acidic.

Advantageously, it proves to be the case that the residual liquid phase, after the extraction, can contain microorganisms M which are living and therefore potentially active. Since, in this liquid phase, there are fewer carboxylic acids than initially, the pH of the liquid phase is less acidic. It is therefore possible to reinject it into the fermentation reactor 1. Thus, not only is the acidosis phenomenon reduced and/or the pH of the fermentation medium stabilized during fermentation, by extraction of the acid compounds but, to a certain extent, the medium is also reinoculated with microorganisms M providing the fermentation, this being without significantly lowering the pH of the fermentation medium.

Such a solution makes it possible to optimize the yield of the fermentation and to carry out a continuous fermentation, this being by reducing the fermentation times, while at the same time tending toward zero waste.

The extraction is carried out continuously or sequentially, for example with an extraction every 12 hours. In other words, it is possible to continue the fermentation while at the same time extracting the metabolites produced, either as they are produced or regularly. Once extracted, the metabolites are purified and/or converted into other products, such as alkanes, alkenes, amides, amines, esters or polymers, by chemical techniques known per se, for instance distillation, synthesis, electrosynthesis, amidation or polymerization.

More specifically, an extraction column 2 is fed with fermentation must at the top of the column, according to the arrow 3. In the column 2, the endogenous solvent, therefore a carboxylic acid or a mixture of carboxylic acids, is injected beforehand. As previously mentioned, the endogenous solvent is advantageously a carboxylic acid having seven or eight carbons. As it happens, the amount produced by the fermentation is not generally sufficient to ensure extraction of the majority of the other carboxylic acids produced. It is therefore necessary to introduce such carboxylic acids originating from a source other than the ongoing fermentation. They may, for example, be carboxylic acids previously extracted and stored for this use or else acids, advantageously biobased acids, originating from a commercial source.

A countercurrent circulation or a circulating with stirring, by means known per se, allows the carboxylic acids to be brought into contact with the solvent. During this first step, the carboxylic acids, or at least a part thereof, are transferred into the solvent.

The fermentation must, de facto depleted of carboxylic acids, is collected at the bottom of extraction column 2 and, preferentially, reintroduced into the fermenter 1, according to the arrow 4. Since the solvent is also one of the carboxylic acids present in the fermentation must, no contamination harmful to continuation of the fermentation by the solvent following the reintroduction of the must is possible.

The solvent, with the carboxylic acids that it contains, is collected at the top of the extraction column 2 and, according to the arrow 5, transferred to a first distillation column 6. The solvent and the extracted carboxylic acids form at least one organic phase which is at least partially miscible with water. It is recalled here that the example described and illustrated corresponds to an embodiment with more than one, namely two, distillation columns. Such an embodiment is the one that will be encountered for facilities of "average" sizes.

The distillation is carried out at temperatures which make it possible to selectively recover the carboxylic acids of which the boiling point is lower than that of the solvent.

The carboxylic acids and the water derived from the extraction are collected, at the end of the distillation, at the top of the column 6. This stream is, according to the arrow 7, cooled and directed to a decanter 8.

The solvent, which is collected at the bottom of the column 6, is heavier than the extracted carboxylic acids. The solvent is redirected, according to the arrow 9, to the extraction column 2. Thus, the solvent is reused, while minimizing the losses and limiting the requirements for external introduction of endogenous solvent.

At the end of the decanting, the aqueous phase is collected and sent back, according to the arrow 10, to the extraction column 2.

The constituent carboxylic acids of the organic phase recovered at the bottom of the decanter 8 are therefore a mixture of various carboxylic acids and, optionally, water in proportions requiring, in certain cases, an additional treatment. In other words, with the exception of large facilities such as those encountered in industrial refineries, it will be judicious, in order to optimize the efficiency/cost ratio, to carry out, as illustrated in FIG. 1, an additional distillation. For this, the carboxylic acids are directed, according to the arrow 11 to a second distillation column 12. Thus, a solution comprising essentially only an organic phase is introduced into the distillation column 12.

At the end of the second distillation, the carboxylic acids are collected at the bottom of column 12, the boiling points being higher than that of water, and, according to the arrow 13, directed to a collection and storage member 14. Advantageously, when there are two distillation members, it is advantageous to envision at least one decanting member. As a variant, at least one part of the carboxylic acids collected, purified or as a mixture is directly directed to a member which makes it possible to synthesize final molecules. The water collected at the end of the second distillation is, preferably, according to the arrow 15, directed to the extraction column 2. Moreover, as in the embodiment illustrated in FIG. 1, for non-purified carboxylic acids, it is advantageous to envision another separation, by means of at least one distillation, in order to collect pure products, or products that are at the very least usable. Thus, with successive distillations, each acid can be separated. These various distillations can be carried out in a single distillation member, provided that the latter has a sufficient design and size. In practice, it generally involves distillation columns as encountered in industrial facilities of refinery type.

It is advantageous, according to the distillation conditions, to envision at least one heat exchanger 16 in order to cool the solvent. Advantageously, the heat thus recovered is used to preheat the solvent leaving the top of the extraction column, before it is introduced into the distillation column 6. In this way, it is possible to significantly reduce the consumption of energy required for the first distillation. It is understood that either at least two exchangers are envisioned for these various heat streams, or just one.

In other embodiments, the number and/or the dimensions of the various members are different than those described. In particular, several facilities in parallel may be envisioned.

Likewise, those skilled in the art are able to envision the control and safety members usually encountered in extraction and/or distillation facilities.

Tests have been carried out by the applicant according to various embodiments, in the case of the extraction of carboxylic acids.

Test 1: Extraction with Heptanoic Acid

The carboxylic acids produced during a fermentation that is carried out on a substrate comprising the fermentable fraction of household waste at a concentration of 50 g/l of dry matter (DM). 50 ml of the fermentation medium, therefore the liquid phase, are recovered. The pH of this sample is 4.3. These 50 ml are then subjected to an extraction with heptanoic acid in a 1/1 volume ratio. The extraction yield obtained is 37%.

The applicant noted that, under the same test conditions, an identical yield is obtained when replacing the heptanoic acid with octanoic acid.

Comparative fermentation tests were also carried out by the applicant, according to various embodiments, in order to evaluate the effect of the presence of extraction solvents in the fermentation medium on the fermentation yield.

Test 2: Comparison of Fermentations in the Presence or Absence of Heptanoic Acid Two fermentations of grass cuttings/mowings in non-sterile mode, at a concentration of 25 g/l of dry matter, in an anaerobic bioreactor with a working volume of 2 l, operated in mesophilic mode (38° C.), were carried out in parallel for 160 h. In the first experiment, after inoculation of an optimized anaerobic microbial mix, an initial addition of heptanoic acid in an amount of 2.8 g/l was carried out. This presence of heptanoic acid makes it possible to understand the biocompatible nature of an extraction carried out with this type of solvent. Indeed, the culture medium after extraction is reintroduced into the bioreactor and may contain traces of extraction solvent up to the amount of their solubility threshold. The second fermentation, which is de facto a control culture, was carried out in parallel under the same conditions except for the addition of heptanoic acid.

During these fermentations, liquid-phase and gas-phase metabolite monitorings were carried out. At the end of fermentation, the yields obtained regarding the production of volatile fatty acids is 0.33 g of VFA/g of dry matter in the case of the experiment with the addition of heptanoic acid, and 0.39 g of VFA/g of dry matter for the control fermentation. It is therefore noted that the presence of solvent induces a slightly negative effect, of about 15%, on the production of volatile fatty acids, while at the same time keeping yields above 30%, which is in itself an altogether acceptable value in terms of performance.

The presence of heptanoic acid in the bioreactor generates the same metabolic behavior as an excessive accumulation of volatile fatty acids in the fermentation medium. Lowering the initial concentration of heptanoic acid or choosing a carboxylic acid as solvent having a lower solubility than that of heptanoic acid in the culture medium would make it possible to achieve yields equivalent to those obtained with the control culture. In order to validate this solution, the applicant carried out the following test.

Test 3: Comparison of Fermentation in the Presence or Absence of Octanoic Acid

Test 2 is reproduced with the same culture conditions, but using 50 g/l of dry matter of restoration waste and by this time comparing the yields obtained during a fermentation with an initial addition of 0.7 g/l of octanoic acid compared with a control fermentation experiment which does not contain any octanoic acid.

At the end of fermentation, a yield of 0.3 g of VFA/g of dry matter is obtained in the case of the culture with octanoic acid, and of 0.31 g of VFA/g of dry matter as regards the control culture.

The yields are therefore equivalent and it is concluded that the presence of octanoic acid, at its maximum solubility, does not disrupt the fermentation.

The implementation of such a process involves not only the presence in the facility of at least one fermentation reactor 1, but also the presence of at least one extraction column 2, and at least one, advantageously two, distillation columns 6 and 12, and also of at least one decanter 8 and, in one advantageous embodiment, at least one heat exchanger 16. These members are known per se, their numbers and their dimensions being adjusted to the type of production.

Such a facility advantageously also comprises at least one member for storing the products resulting from the extraction. Management and control means, such as temperature sensors, pH probes and/or redox probes, are envisioned. Moreover, the activity of the microorganisms is monitored by means of methods known per se, for example by analytical monitoring of the production of gas and liquid metabolites, counts by flow cytometry, molecular biological techniques such as molecular imprints or biochips.

The invention claimed is:

1. A process for directly extracting carboxylic acids having from one to nine carbons, produced by a mixture of eukaryotic and prokaryotic microorganisms in a fermentation reactor by anaerobic fermentation of an untreated fermentable biomass, said extraction being of a liquid-liquid type, without significantly lowering pH of a fermentation medium, said process comprising:

a) initiating the extraction process when production of the carboxylic acids having from one to nine carbons reaches a predefined amount in the fermentation reactor, the predefined amount corresponding to a slowing of growth of the eukaryotic and prokaryotic microorganisms in the fermentation reactor, the slowing of growth lying in a region of microorganism inhibition threshold linked to an acidification of the fermentation medium, b) choosing an endogenous extraction solvent among carboxylic acids having at least four carbons produced during the anaerobic fermentation of the untreated fermentable biomass, such that the number of carbons of the endogenous extraction solvent is greater than or equal to the number of carbons of the carboxylic acids to be extracted, wherein the endogenous extraction solvent has a density below that of water and a boiling point above 70° C. under normal pressure conditions, c) bringing the endogenous extraction solvent into contact with a portion of fermentation medium from the fermentation reactor containing at least the carboxylic acids having from one to nine carbons outside the fermentation reactor, without halting the fermentation inside the fermentation reactor, d) directly extracting the carboxylic acids having from one to nine carbons from the fermentation medium through contact with the endogenous extraction solvent under conditions which are non-lethal for the eukaryotic and prokaryotic microorganisms, e) separating the carboxylic acids having from one to nine carbons from the endogenous extraction solvent, obtained after liquid-liquid type extraction at step d), through at least one distillation, f) collecting and storing or using the carboxylic acids having from one to nine carbons obtained in step e), wherein directly extracting the carboxylic acids in step d) reduces the acidification of the fermentation medium during the anaerobic fermentation, which maintains activity of the eukaryotic and prokaryotic microorganisms in the fermentation reactor for continuing the anaerobic fermentation.

2. The process as claimed in claim 1, wherein, after step e) and before step f), carboxylic acids are separated by distillation during an additional step g), from water of an organic phase obtained in step e).

3. The process as claimed in claim 1, wherein the extraction solvent is a carboxylic acid having from four to nine carbons.

4. The process as claimed in claim 3, wherein the extraction solvent is a carboxylic acid having seven or eight carbons.

5. The process as claimed in claim 1, wherein the extraction solvent is chosen from heptanoic acid, octanoic acid or nonanoic acid.

6. The process as claimed in claim 1, wherein a decanting step h), between steps e) and f), allows a first separation between organic and aqueous phases.

7. The process as claimed in claim 1, wherein, during the bringing of the fermentation medium into contact with the extraction solvent outside the reactor, the fermentation medium is taken continuously.

8. The process as claimed in claim 1, wherein, during the bringing of the fermentation medium into contact with the extraction solvent outside the reactor, the fermentation medium is taken sequentially.

9. The process as claimed in claim 1, wherein, after step e), at least one part of a residual liquid phase resulting from the extraction, containing active microorganisms, is reintroduced into the fermentation reactor and incorporated into the fermentation medium without significantly lowering the pH of the fermentation medium.

* * * * *